(12) United States Patent
Mahajan et al.

(10) Patent No.: US 8,744,556 B2
(45) Date of Patent: Jun. 3, 2014

(54) NOISE DETECTION IN IMPLANTABLE MEDICAL DEVICES

(75) Inventors: Deepa Mahajan, Circle Pines, MN (US); David L. Perschbacher, Coon Rapids, MN (US); LeAnne M. Eberle, Mahtomedi, MN (US); Yanting Dong, Lexington, KY (US); Vijay Aditya Tadipatri, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 169 days.

(21) Appl. No.: 13/357,085

(22) Filed: Jan. 24, 2012

(65) Prior Publication Data

US 2012/0203123 A1 Aug. 9, 2012

Related U.S. Application Data

(60) Provisional application No. 61/439,454, filed on Feb. 4, 2011.

(51) Int. Cl.
*A61B 5/0402* (2006.01)

(52) U.S. Cl.
USPC .......................................... 600/509; 600/522

(58) Field of Classification Search
USPC ................................. 600/509, 522
See application file for complete search history.

(56) References Cited

U.S. PATENT DOCUMENTS

| | | | |
|---|---|---|---|
| 4,432,362 A | 2/1984 | Leckrone et al. | |
| 4,589,420 A | 5/1986 | Adams et al. | |
| 4,779,617 A | 10/1988 | Whigham | |
| 4,913,146 A | 4/1990 | DeCote, Jr. | |
| 4,960,123 A | 10/1990 | Maker | |
| 5,010,887 A | 4/1991 | Thornander | |
| 5,188,117 A | 2/1993 | Steinhaus et al. | |
| 5,209,237 A | 5/1993 | Rosenthal | |

(Continued)

FOREIGN PATENT DOCUMENTS

| EP | 1656182 | 2/2010 |
|---|---|---|
| JP | 2002518110 | 6/2002 |

(Continued)

OTHER PUBLICATIONS

Gunderson, Bruce D, et al., "Automatic Identification of Clinical Lead Dysfunctions", PACE, vol. 28, (Jan. 2005), S63-S67.

(Continued)

*Primary Examiner* — Christopher D Koharski
*Assistant Examiner* — Michael Carey
(74) *Attorney, Agent, or Firm* — Schwegman, Lundberg & Woessner, P.A.

(57) ABSTRACT

An apparatus comprises a primary cardiac signal sensing circuit configured to sense at least a first cardiac signal, a secondary cardiac signal sensing circuit configured to sense a secondary cardiac signal, and a control circuit. The control circuit includes a noise detection circuit that has an alignment circuit. The alignment circuit is configured to align a segment of the sensed first cardiac signal with a segment of the sensed secondary cardiac signal. The noise detection circuit configured to determine a number of turns in the first cardiac signal segment, determine a number of turns in the secondary cardiac signal segment, generate an indication of noise in the first and secondary cardiac signals according to the determined number of turns, and provide the indication of noise to a user or process.

18 Claims, 9 Drawing Sheets

(56) References Cited

U.S. PATENT DOCUMENTS

| | | | |
|---|---|---|---|
| 5,370,124 | A | 12/1994 | Dissing et al. |
| 5,492,128 | A | 2/1996 | Wickham |
| 5,496,350 | A | 3/1996 | Lu |
| 5,522,857 | A | 6/1996 | van Krieken |
| 5,558,098 | A | 9/1996 | Fain |
| 5,562,713 | A | 10/1996 | Silvian |
| 5,564,430 | A | 10/1996 | Jacobson et al. |
| 5,573,550 | A | 11/1996 | Zadeh et al. |
| 5,613,495 | A | 3/1997 | Mills et al. |
| 5,697,958 | A | 12/1997 | Paul et al. |
| 5,702,425 | A | 12/1997 | Wickham |
| 5,702,427 | A | 12/1997 | Ecker et al. |
| 5,709,215 | A | 1/1998 | Perttu et al. |
| 5,755,738 | A | 5/1998 | Kim et al. |
| 5,766,227 | A | 6/1998 | Nappholz et al. |
| 5,776,168 | A | 7/1998 | Gunderson |
| 5,778,881 | A | 7/1998 | Sun et al. |
| 5,782,876 | A | 7/1998 | Flammang |
| 5,792,212 | A | 8/1998 | Weijand |
| 5,817,130 | A | 10/1998 | Cox et al. |
| 5,817,135 | A | 10/1998 | Cooper et al. |
| 5,861,008 | A | 1/1999 | Obel et al. |
| 5,865,749 | A | 2/1999 | Doten et al. |
| 5,867,361 | A | 2/1999 | Wolf et al. |
| 5,870,272 | A | 2/1999 | Seifried et al. |
| 5,891,171 | A | 4/1999 | Wickham |
| 5,897,575 | A | 4/1999 | Wickham |
| 5,957,857 | A | 9/1999 | Hartley |
| 5,978,710 | A | 11/1999 | Prutchi et al. |
| 5,999,848 | A | 12/1999 | Gord et al. |
| 6,029,086 | A | 2/2000 | Kim et al. |
| 6,031,710 | A | 2/2000 | Wolf et al. |
| 6,063,034 | A | 5/2000 | Doten et al. |
| 6,068,589 | A | 5/2000 | Neukermans |
| 6,112,119 | A | 8/2000 | Schuelke et al. |
| 6,195,585 | B1 | 2/2001 | Karunasiri et al. |
| 6,198,968 | B1 | 3/2001 | Prutchi et al. |
| 6,201,993 | B1 | 3/2001 | Kruse et al. |
| 6,208,900 | B1 | 3/2001 | Ecker et al. |
| 6,223,078 | B1 | 4/2001 | Marcovecchio |
| 6,223,083 | B1 | 4/2001 | Rosar |
| 6,230,059 | B1 | 5/2001 | Duffin |
| 6,236,882 | B1 | 5/2001 | Lee et al. |
| 6,282,446 | B1 | 8/2001 | Eberle et al. |
| 6,321,115 | B1 | 11/2001 | Mouchawar et al. |
| 6,381,494 | B1 | 4/2002 | Gilkerson et al. |
| 6,473,649 | B1 | 10/2002 | Gryzwa et al. |
| 6,505,071 | B1 | 1/2003 | Zhu et al. |
| 6,597,942 | B1 | 7/2003 | Yonce et al. |
| 6,599,242 | B1 | 7/2003 | Splett et al. |
| 6,684,100 | B1 | 1/2004 | Sweeney et al. |
| 6,708,058 | B2 | 3/2004 | Kim et al. |
| 6,745,076 | B2 | 6/2004 | Wohlgemuth et al. |
| 6,754,527 | B2 | 6/2004 | Stroebel et al. |
| 6,782,291 | B1 | 8/2004 | Bornzin et al. |
| 6,839,587 | B2 | 1/2005 | Yonce |
| 6,862,476 | B2 | 3/2005 | Mouchawar et al. |
| 6,892,092 | B2 | 5/2005 | Palreddy et al. |
| 6,917,830 | B2 | 7/2005 | Palreddy et al. |
| 6,950,702 | B2 | 9/2005 | Sweeney |
| 6,985,768 | B2 | 1/2006 | Hemming et al. |
| 7,027,858 | B2 | 4/2006 | Cao et al. |
| 7,031,764 | B2 | 4/2006 | Schwartz et al. |
| 7,155,275 | B2 | 12/2006 | Linder et al. |
| 7,215,993 | B2 | 5/2007 | Lin |
| 7,233,827 | B1 | 6/2007 | Bornzin et al. |
| 7,248,921 | B2 | 7/2007 | Palreddy et al. |
| 7,289,845 | B2 | 10/2007 | Sweeney et al. |
| 7,467,009 | B2 * | 12/2008 | Palreddy et al. .......... 600/509 |
| 7,500,955 | B2 | 3/2009 | Sweeney |
| 7,515,955 | B2 | 4/2009 | Linder et al. |
| 7,567,835 | B2 | 7/2009 | Gunderson et al. |
| 7,650,182 | B2 | 1/2010 | Kim et al. |
| 7,792,571 | B2 | 9/2010 | Sweeney et al. |
| 8,078,272 | B2 | 12/2011 | Lin |
| 8,521,276 | B2 | 8/2013 | Sweeney et al. |
| 2003/0083713 | A1 | 5/2003 | Palreddy |
| 2004/0030256 | A1 | 2/2004 | Lin |
| 2004/0106957 | A1 | 6/2004 | Palreddy et al. |
| 2005/0192504 | A1 | 9/2005 | Palreddy et al. |
| 2005/0288600 | A1 | 12/2005 | Zhang et al. |
| 2006/0224075 | A1 | 10/2006 | Gunderson et al. |
| 2006/0247695 | A1 | 11/2006 | Stalsberg et al. |
| 2007/0135722 | A1 | 6/2007 | Lin |
| 2007/0203419 | A1 | 8/2007 | Sweeney et al. |
| 2008/0161872 | A1 | 7/2008 | Gunderson |
| 2008/0172098 | A1 | 7/2008 | Gunderson et al. |
| 2008/0228093 | A1 | 9/2008 | Dong et al. |
| 2009/0093731 | A1 | 4/2009 | Palreddy et al. |
| 2009/0192395 | A1 | 7/2009 | Sweeney |
| 2009/0264716 | A1 | 10/2009 | Shuros et al. |
| 2010/0106209 | A1 | 4/2010 | Gunderson et al. |
| 2010/0204745 | A1 | 8/2010 | Li et al. |
| 2010/0305645 | A1 | 12/2010 | Sweeney et al. |
| 2011/0172729 | A1 | 7/2011 | Sweeney et al. |

FOREIGN PATENT DOCUMENTS

| | | |
|---|---|---|
| WO | WO-9965565 | 12/1999 |
| WO | WO-0143820 A1 | 6/2001 |
| WO | WO-2005018738 A1 | 3/2005 |
| WO | WO-2011088043 A1 | 7/2011 |

OTHER PUBLICATIONS

Rhude, Jennifer, et al., "New ICD Algorithm to Detect Lead Failure Noise and Prevent Inappropriate Therapy", Heart Rhythm, vol. 7, No. 5, PO5-127, (May 2010), S364-S365.

"U.S. Appl. No. 10/046,650, Non-Final Office Action mailed Jun. 24, 2004", 9 pgs.

"U.S. Appl. No. 10/046,650, Response filed Sep. 28, 2004 to Non-Final Office Action mailed Jun. 24, 2004", 12 pgs.

"U.S. Appl. No. 10/213,364, Final Office Action mailed May 12, 2006", 10 pgs.

"U.S. Appl. No. 10/213,364, Final Office Action mailed Jul. 27, 2006", 12 pgs.

"U.S. Appl. No. 10/213,364, Final Office Action mailed Oct. 14, 2005", 9 pgs.

"U.S. Appl. No. 10/213,364, Non-Final Office Action mailed Feb. 7, 2006", 8 pgs.

"U.S. Appl. No. 10/213,364, Non-Final Office Action mailed May 25, 2005", 7 pgs.

"U.S. Appl. No. 10/213,364, Notice of Allowance mailed Oct. 4, 2006", 7 pgs.

"U.S. Appl. No. 10/213,364, Response filed Jan. 13, 2006 to Advisory Action mailed Jan. 9, 2006", 12 pgs.

"U.S. Appl. No. 10/213,364, Response filed May 8, 2006 to Non-Final Office Action mailed Feb. 7, 2006", 12 pgs.

"U.S. Appl. No. 10/213,364, Response filed Jul. 12, 2006 to Final Office Action mailed May 12, 2006", 12 pgs.

"U.S. Appl. No. 10/213,364, Response filed Sep. 20, 2005 to Non-Final Office Action mailed May 25, 2005", 10 pgs.

"U.S. Appl. No. 10/213,364, Response filed Sep. 27, 2006 to Final Office Action mailed Jul. 27, 2006", 11 pgs.

"U.S. Appl. No. 10/213,364, Response filed Dec. 12, 2005 to Final Office Action mailed Oct. 14, 2005", 11 pgs.

"U.S. Appl. No. 10/643,770, Non-Final Office Action mailed Jun. 24, 2004", 7 pgs.

"U.S. Appl. No. 10/643,770, Response filed Oct. 25, 2004 to Non Final Office Action mailed Jun. 24, 2004", 11 pgs.

"U.S. Appl. No. 11/110,490, Non-Final Office Action mailed Mar. 14, 2008", 8 pgs.

"U.S. Appl. No. 11/110,490, Response filed Jun. 3, 2008 to Non Final Office Action mailed Mar. 14, 2008", 12 pgs.

"U.S. Appl. No. 11/625,432, Non-Final Office Action mailed May 10, 2010", 9 pgs.

"U.S. Appl. No. 11/625,432, Non-Final Office Action mailed Oct. 26, 2010", 7 pgs.

"U.S. Appl. No. 11/625,432, Response filed Jan. 28, 2010 to Restriction Requirement mailed Dec. 31, 2009", 10 pgs.

(56) References Cited

OTHER PUBLICATIONS

"U.S. Appl. No. 11/625,432, Response filed Feb. 28, 2011 to Non-Final Office Action mailed Oct. 26, 2010", 10 pgs.

"U.S. Appl. No. 11/625,432, Response filed Aug. 10, 2010 to Non-Final Office Action mailed May 10, 2010", 11 pgs.

"U.S. Appl. No. 12/333,008, Non-Final Office Action mailed Oct. 12, 2011", 11 pgs.

"European Application Serial No. 03767175.7, Office Action mailed Mar. 11, 2005", 5 pgs.

"European Application Serial No. 03767175.7, Response filed Sep. 21, 2010 to Office Action mailed Mar. 11, 2010", 13 pgs.

"International Application Serial No. PCT/US2004/026993, International Search Report mailedNov. 18, 2004", 3 pgs.

"International Application Serial No. PCT/US2011/020834, International Search Report mailed May 4, 2011", 4 pgs.

"International Application Serial No. PCT/US2011/020834, Written Opinion mailed May 4, 2011", 9 pgs.

"Japanese Application Serial No. 2004-526424, Office Action mailed May 26, 2009" (with English Translation), 5 pgs.

"Japanese Application Serial No. 2006-524060, Office Action mailed May 16, 2010" (with English Translation), 5 pgs.

Gunderson, Bruce, "Automatic Identification of ICD Lead Problems Using Electrograms", PACE, vol. 24, p. 664, Apr. 2002, (2002), 664.

Morris, W., "American Heritage Dictionary—2nd Edition", Boston: Houghton Mifflin, Property of U.S. Government, (1982), 74, 269, and 283.

Palreddy, Surekha, "File History for U.S. Appl. No. 10/046,650", 34 pgs.

Palreddy, Surekha, "File History U.S. Appl. No. 11/110,490", 24 pgs.

Sweeney, Robert J, et al., "Significant point algorithm for tachyarrhythmia detection", Heart Rhythm, vol. 1(No. 1, Supp. 1), (May, 2004), S80.

"U.S. Appl. No. 13/004,582, Final Office Action mailed Mar. 6, 2013", 22 pgs.

"U.S. Appl. No. 13/004,582, Notice of Allowance mailed May 1, 2013", 8 pgs.

"U.S. Appl. No. 13/004,582, Response filed Mar. 29, 2013 to Final Office Action mailed Mar. 6, 2013", 10 pgs.

"U.S. Appl. No. 13/004,582, Response filed Oct. 4, 2013 to Non Final Office Action mailed Jul. 5, 2012", 23 pgs.

"International Application Serial No. PCT/US2011/020834, International Preliminary Report on Patentability mailed Jul. 26, 2012", 10 pgs.

* cited by examiner

NON-NOISY

$$conf = \exp\frac{-(t-8)^2}{25}$$

| # TURNS (RV) | CONF. |
|---|---|
| < 5 | < 52.7 |
| 5 | 69.7 |
| 6 | 85.2 |
| 7 | 96.1 |
| 8 | 100 |
| 9 | 96.1 |
| 10 | 85.2 |
| 11 | 69.7 |
| > 11 | < 52.7 |

NOISY RV

$$conf = 1 - \exp\frac{-(t-17.5)^2}{6}$$

| # TURNS (RV) | CONF. |
|---|---|
| 18 | 4.1 |
| 19 | 31.2 |
| 20 | 64.7 |
| 21 | 87 |
| > 21 | > 96.5 |

NOISY SHOCK

$$conf = 1 - \exp\frac{-(t-12.5)^2}{6}$$

| # TURNS (SH) | CONF. |
|---|---|
| 13 | 4.1 |
| 14 | 31.2 |
| 15 | 64.7 |
| 16 | 87 |
| > 16 | > 96.5 |

*FIG. 10*

NOISE DETECTION IN IMPLANTABLE MEDICAL DEVICES

CROSS-REFERENCE TO RELATED APPLICATION

This application claims the benefit of priority of U.S. Provisional Application No. 61/439,454, filed on Feb. 4, 2011, under 35 U.S.C. §119(e), which is hereby incorporated by reference in its entirety.

BACKGROUND

Ambulatory medical devices include implantable medical devices (IMDs) and wearable medical devices (WMDs). Some examples of IMDs include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

WMDs include wearable cardioverter defibrillators (WCDs) and wearable diagnostic devices. WCDs can be monitoring devices that include surface electrodes. The surface electrodes are arranged to provide one or both of monitoring to provide surface electrocardiograms (ECGs) and delivering cardioverter and defibrillator shock therapy.

Some medical devices detect events by monitoring electrical heart activity signals. In CFM devices, these events can include heart chamber expansions or contractions. By monitoring cardiac signals indicative of expansions or contractions, medical devices can detect abnormally slow heart rate, or bradycardia. Some medical devices detect abnormally rapid heart rate, or tachyarrhythmia. Tachyarrhythmia includes ventricular tachycardia (VT) and supraventricular tachycardia (SVT). Tachyarrhythmia also includes rapid and irregular heart rate, or fibrillation, including ventricular fibrillation (VF).

Treatment of cardiac disease with medical devices may be complicated due to over-sensing by sense-amplifiers. Over-sensing occurs when sense-amplifiers incorrectly interpret sensed signals or noise as cardiac signal artifacts, such as P or R-waves indicative of atrial or ventricular heart contractions respectively. Over-sensing can result in a bradycardia device incorrectly inhibiting pacing therapy or a tachyarrhythmia device incorrectly delivering high energy shock therapy. The present inventors have recognized a need for improved sensing of events related to cardiac activity.

An example of a method of curvature based classification of cardiac signals can be found in Sweeney et al., "Curvature Based Methods for Selecting Features From Electrophysiologic Signals for Purpose of Identification and Classification," U.S. Pat. No. 6,684,100, filed Oct. 31, 2000. An example of a method of determining whether noise is present on a cardiac signal based on a moving count of turning/inflection points can be found in Palreddy et al., "Cardiac Rhythm Management System With Noise Detector Utilizing a Hysteresis Providing Threshold," U.S. Pat. No. 6,892,092, filed Oct. 29, 2001.

Overview

This document relates generally to systems, devices, and methods for monitoring cardiac electrophysiological parameters of a patient or subject. Episodes of atrial and ventricular tachyarrhythmia are also monitored.

An apparatus example includes a primary cardiac signal sensing circuit configured to sense at least a first cardiac signal, a secondary cardiac signal sensing circuit configured to sense a secondary cardiac signal, and a control circuit. The control circuit includes a noise detection circuit that has an alignment circuit. The alignment circuit is configured to align a segment of the sensed first cardiac signal with a segment of the sensed secondary cardiac signal. The noise detection circuit is configured to determine a number of turns in the first cardiac signal segment, determine a number of turns in the secondary cardiac signal segment, generate an indication of noise in the first and secondary cardiac signals according to the determined number of turns, and provide the indication of noise to a user or process.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 10 shows an example of confidence levels for a noise classification.

DETAILED DESCRIPTION

This document discusses systems and methods for improved detection of cardiac events by an ambulatory medical device. Specifically systems and methods for improved discrimination or classification of tachyarrhythmia by a medical device are described.

An ambulatory medical device may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

The efficacy of a medical device in treating abnormally rapid heart rates is often expressed in terms of sensitivity and specificity. Sensitivity refers to the ability of the detection scheme of a device to effectively detect an abnormal heart rhythm that the device is to treat (e.g., ventricular tachycardia or ventricular fibrillation, or to distinguish these abnormal rhythms from noise). Specificity refers to the ability of the detection scheme of a device to avoid treating those rhythms that the device is not intended to treat (e.g., sinus tachycardia).

As noted previously, a medical device used in the treatment or the diagnosis of cardiac arrhythmias can be susceptible to over-sensing or under-sensing that may cause the medical device to incorrectly respond to a patient's needs. Noise in an electronic medical system can complicate identification of cardiac arrhythmia. Improved identification of noise can result in detecting tachyarrhythmia with higher sensitivity and higher specificity.

Figure 1:
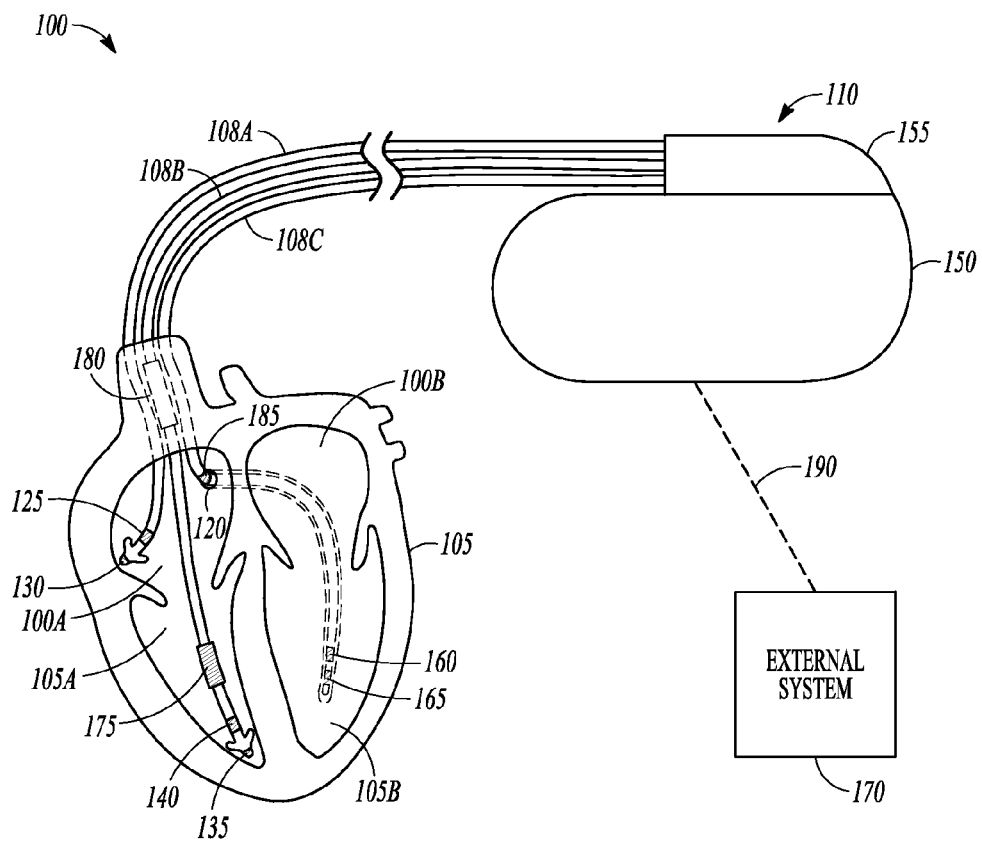
FIG. 1 is an illustration of portions of a system that uses an IMD.

FIG. 1 is an illustration of portions of a system that uses an IMD 110 or other ambulatory medical device. Examples of IMD 110 include, without limitation, a pacemaker, a defibrillator, a cardiac resynchronization therapy (CRT) device, a monitoring/diagnostic device, or a combination of such devices. The system also typically includes an IMD programmer or other external device 170 that communicates wireless signals 190 with the IMD 110, such as by using radio frequency (RF) or other telemetry signals.

The IMD 110 can be coupled by one or more leads 108A-C to heart 105. Cardiac leads 108A-C include a proximal end that coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes can be electrically coupled to sense amplifiers to sense electrical cardiac signals.

Sensed electrical cardiac signals can be sampled to create an electrogram. An electrogram can be analyzed by the IMD and/or can be stored in the IMD and later communicated to an external device where the sampled signals can be displayed for analysis.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation.

The IMD 110 can include a third cardiac lead 108C attached to the IMD 110 through the header 155. The third cardiac lead 108C includes ring electrodes 160 and 165 placed in a coronary vein lying epicardially on the left ventricle (LV) 105B. The third cardiac lead 108C can include a ring electrode 185 positioned near the coronary sinus (CS) 120. Lead 108C optionally provides resynchronization therapy to the heart 105. Resynchronization therapy is typically delivered to the ventricles in order to better synchronize the timing of depolarizations between ventricles.

Lead 108B can include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy can be delivered from the first or RV coil 175 to the second or SVC coil 180. In some examples, the SVC coil 180 can be electrically tied to an electrode formed on the hermetically-sealed IMD housing or can 150. This improves defibrillation by delivering current from the RV coil 175 more uniformly over the ventricular myocardium. In some examples, the therapy can be delivered from the RV coil 175 only to the electrode formed on the IMD can 150.

Note that although a specific arrangement of leads and electrodes are shown in the illustration, an IMD can be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). The present methods and systems will work in a variety of configurations and with a variety of electrodes. Other forms of electrodes include meshes and patches which can be applied to portions of heart 105 or which can be implanted in other areas of the body to help "steer" electrical currents produced by IMD 110.

Figure 2:
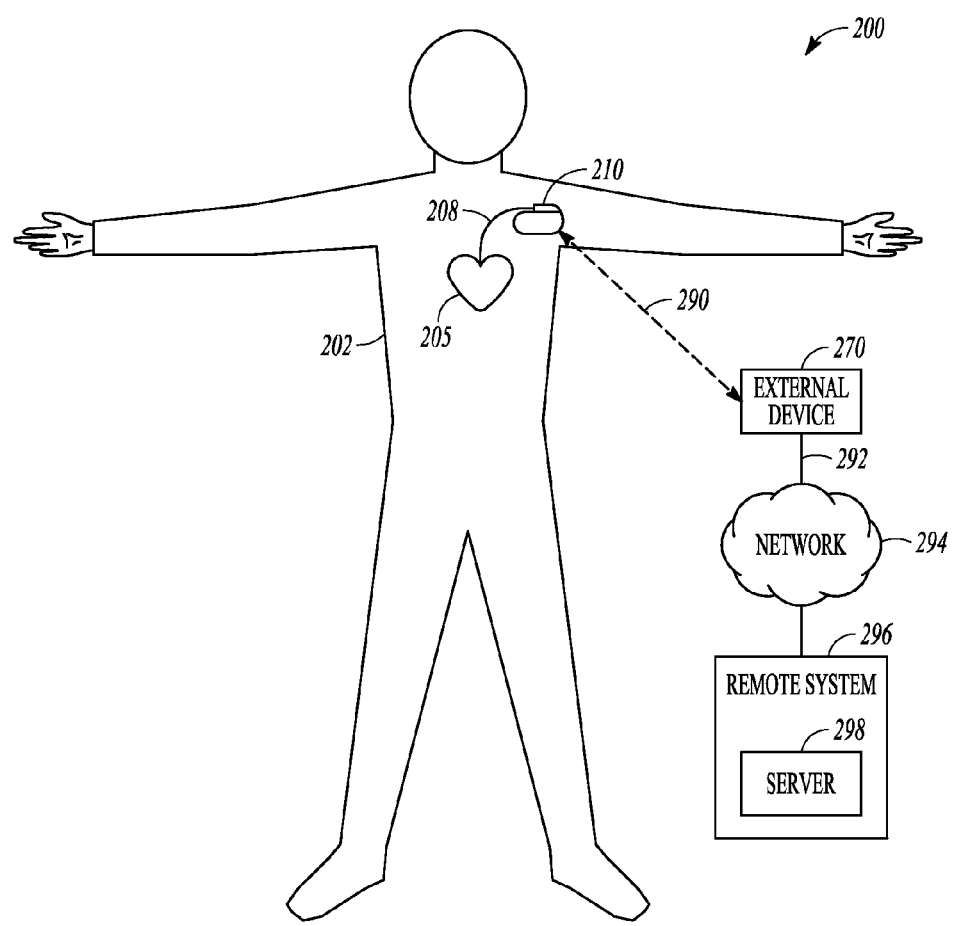
FIG. 2 is an illustration of portions of another system that uses an IMD or other ambulatory medical device.

FIG. 2 is an illustration of portions of another system 200 that uses an IMD or other ambulatory medical device 210 to provide a therapy to a patient 202. The system 200 typically includes an external device 270 that communicates with a remote system 296 via a network 294. The network 294 can be a communication network such as a phone network or a computer network (e.g., the internet). In some examples, the external device includes a repeater and communicates via the network using a link 292 that can be wired or wireless. In some examples, the remote system 296 provides patient management functions and can include one or more servers 298 to perform the functions.

Typically, cardioverter defibrillators detect tachyarrhythmia by first detecting a rapid heart rate. Detection enhancements are sometime used to further distinguish or classify the detected arrhythmia. A detection enhancement example includes determining whether the rate detected in a ventricle (V Rate) is greater than the rate detected in an atrium (A Rate) by a specified rate threshold (e.g., V Rate>A Rate by more than ten beats per minute, or 10 bpm). This is often an indication that the arrhythmia is VT. However, sometimes the enhancements fail to accurately distinguish sensing noise from sensing a tachyarrhythmia.

Figure 3:
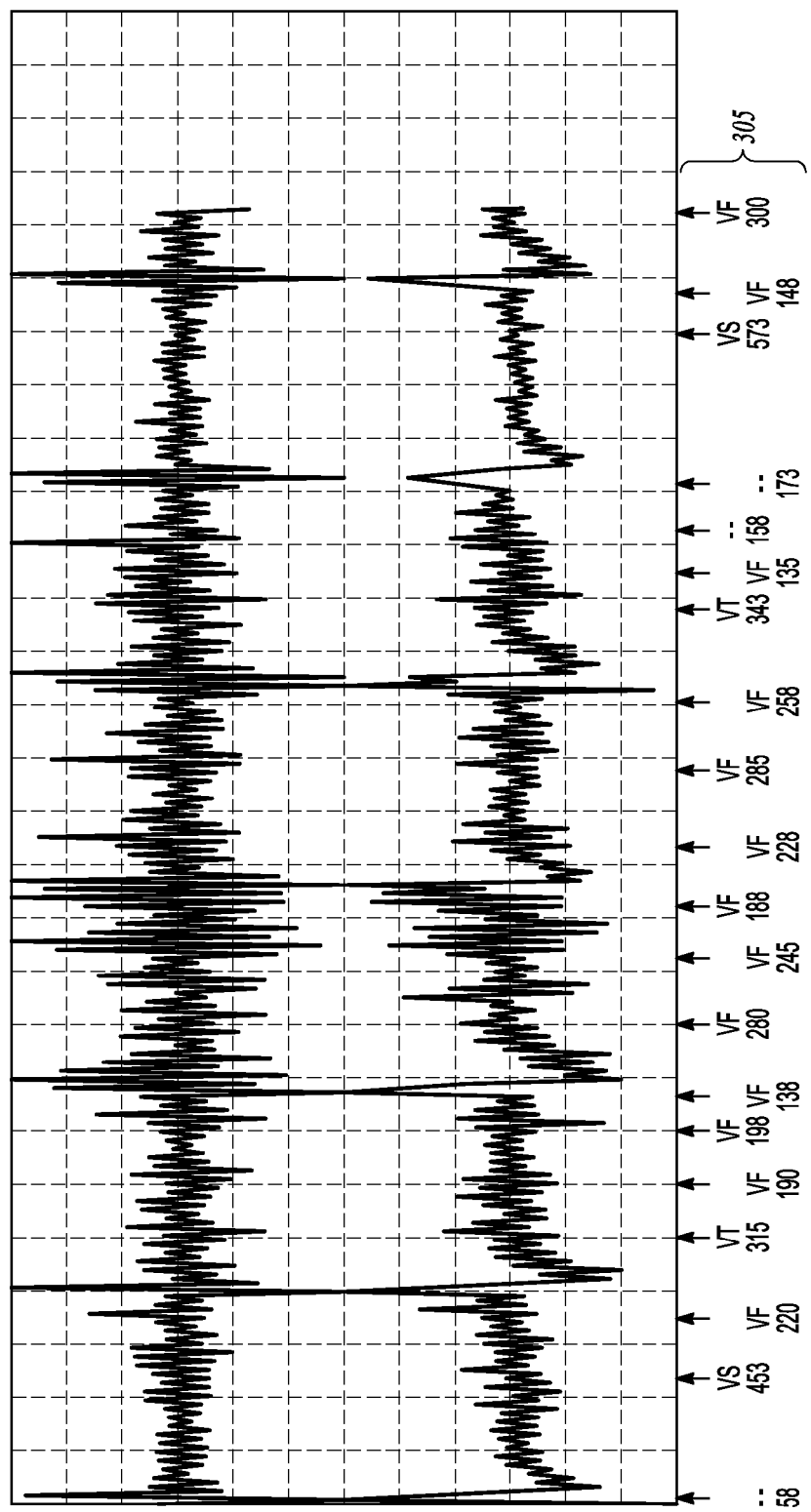
FIG. 3 shows an example of inappropriate therapy delivered due to signal noise.

FIG. 3 shows an example of inappropriate therapy delivered due to signal noise. The markers 305 show that noise on the signals is interpreted as VT and VF. The shock therapy indicated by the markers 305 is an inappropriate delivery of therapy in the presence of noise.

Figure 4:
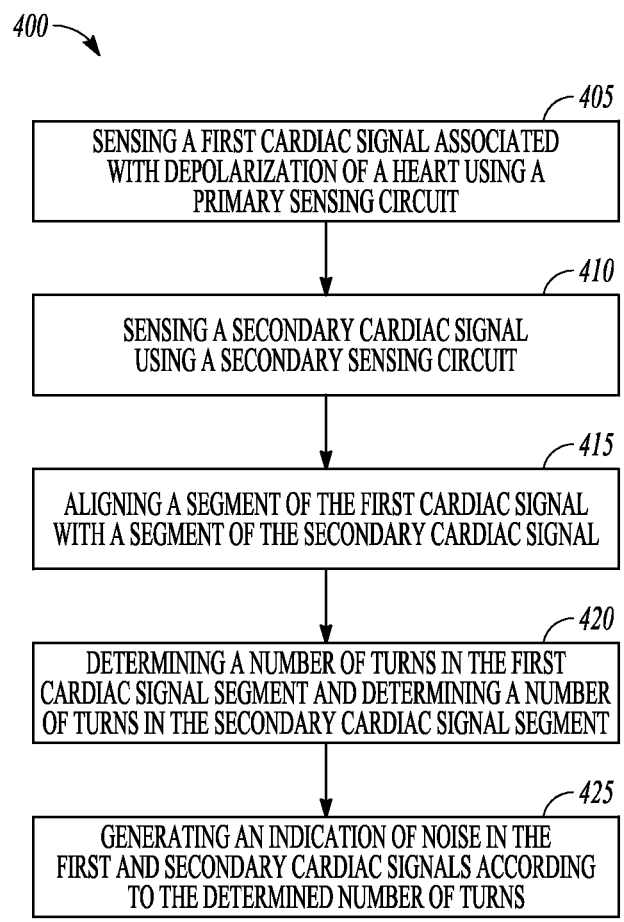
FIG. 4 is a flow diagram of an example of a method of identifying noise in sensed cardiac signals.

FIG. 4 is a flow diagram of an example of a method 400 of identifying noise in cardiac signals that are sensed using an implantable or other ambulatory medical device. At block 405, a first cardiac signal associated with depolarization of a heart of a subject is sensed using a primary sensing circuit. At block 410, a secondary cardiac signal is sensed using a secondary sensing circuit.

As a non-limiting example, the primary sensing circuit may be electrically coupled to the ring electrode 140 and tip electrode 135 shown in the example of FIG. 1. This combination of electrodes can be referred to as an RV sense channel or RV channel. The secondary sensing circuit may be electrically coupled to ring electrode 140 and a can electrode, or to RV coil 175 and the can electrode.

Because the ring electrode 140 and tip electrode 135 can be used to monitor heart rate, the combination of electrodes can also be referred to as a rate channel. A sensing circuit that includes an electrode used to deliver cardioversion or defibrillation therapy can be referred to as a shock channel. When the sensing circuits include different electrodes, the first cardiac signal may be sensed in a different direction than the secondary cardiac signal. Because of the different directions, sensing with different electrodes is sometimes called sensing with different sense vectors.

At block 415, a segment of the first cardiac signal is aligned with a segment of the secondary cardiac signal. This can be necessary because of the time difference in a cardiac signal reaching different combinations of electrodes. Alignment of the cardiac signal segments typically includes aligning sampled signal data using a fiducial marker (e.g., an R-wave representative of depolarization of the ventricles). An assessment of noise is then made in the aligned cardiac signal segments.

At block 420, a number of turns in the first cardiac signal segment is determined and a number of turns in the secondary cardiac signal segment is determined. In some examples, a turn is defined as a change in the cardiac signal from the positive direction to the negative direction, or from the negative direction to the positive direction. In some examples, the cardiac signal segments include a heartbeat of the subject and the number of turns in the signal segments are the number of turns per heartbeat. A determination of noise in the cardiac signals is then made based on the number of turns identified in the cardiac signal segments.

In some examples, the assessment of noise is made from the result of the alignment process. For instance, if the alignment process fails, the cardiac signal segments may be deemed to be noisy.

At block 425, an indication of noise in the first and secondary cardiac signals is generated according to at least one of the determined number of turns or the result of alignment the signals. The indication of noise can be provided to a user or process.

Figure 5:
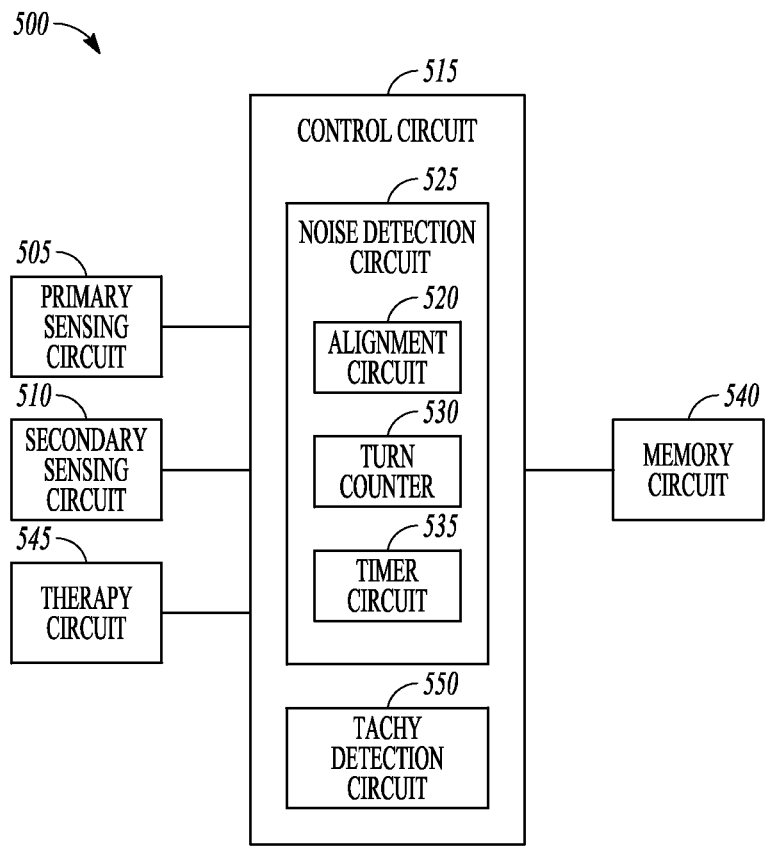
FIG. 5 is block diagram of portions of an example of an implantable or other ambulatory medical that can identify noise in sensed cardiac signals.

FIG. 5 is block diagram of portions of an example of an implantable or other ambulatory medical device 500 that can identify noise in sensed cardiac signals. The device 500 includes at least a primary cardiac signal sensing circuit 505 configured to sense at least a first cardiac signal associated with cardiac depolarization and a secondary cardiac signal sensing circuit 510 configured to sense a second intrinsic cardiac signal. The device 500 can include more than two sensing circuits.

The primary sensing circuit 505 includes at least a first and a second implantable or wearable electrode. The secondary sensing circuit 510 includes at least a third electrode that is different from the first and second electrode. In some examples, the first and second electrodes are configured to sense a cardiac signal of a ventricle (e.g., ring electrodes 160 and 165 in FIG. 1), and the third electrode is configured to provide at least one of cardioversion or defibrillation electrical shock therapy (e.g., RV coil electrode 175).

In some examples, the first and second electrodes are configured to sense a cardiac signal of a right ventricle (e.g., tip electrode 135 and ring electrode 140 in FIG. 1), and the third electrode is configured to sense a cardiac signal of a left ventricle (e.g., ring electrode 160). In some examples, the first and second electrodes are configured to sense a cardiac signal within a heart chamber and the third electrode is configured on a housing of the medical device.

The device 500 also includes a control circuit 515 communicatively coupled to the primary and secondary cardiac signal sensing circuits. The communicative coupling allows electrical signals to be communicated between the primary and secondary sensing circuits and the control circuit 515 even though there may be one or more intervening circuits between the sensing circuits and the control circuit 515. For example, the device 500 may include a sampling circuit (not shown) integral to the control circuit 515 or electrically coupled between the sensing circuits and the control circuit 515. The sampling circuit can sample the first and secondary signals to produce cardiac signal data.

The control circuit 515 can include a processor such as a microprocessor, a digital signal processor, application specific integrated circuit (ASIC), or other type of processor, interpreting or executing instructions in software modules or firmware modules. The control circuit 515 includes other circuits or sub-circuits to perform the functions described. These circuits may include software, hardware, firmware or any combination thereof. Multiple functions can be performed in one or more of the circuits or sub-circuits as desired.

The control circuit 515 includes a noise detection circuit 525. The noise detection circuit 525 includes an alignment circuit 520 that aligns a segment of the sensed first cardiac signal with a segment of the sensed secondary cardiac signal. To align the signal segments, the alignment circuit 520 is configured to identify a depolarization in the first cardiac signal segment.

Figure 6:
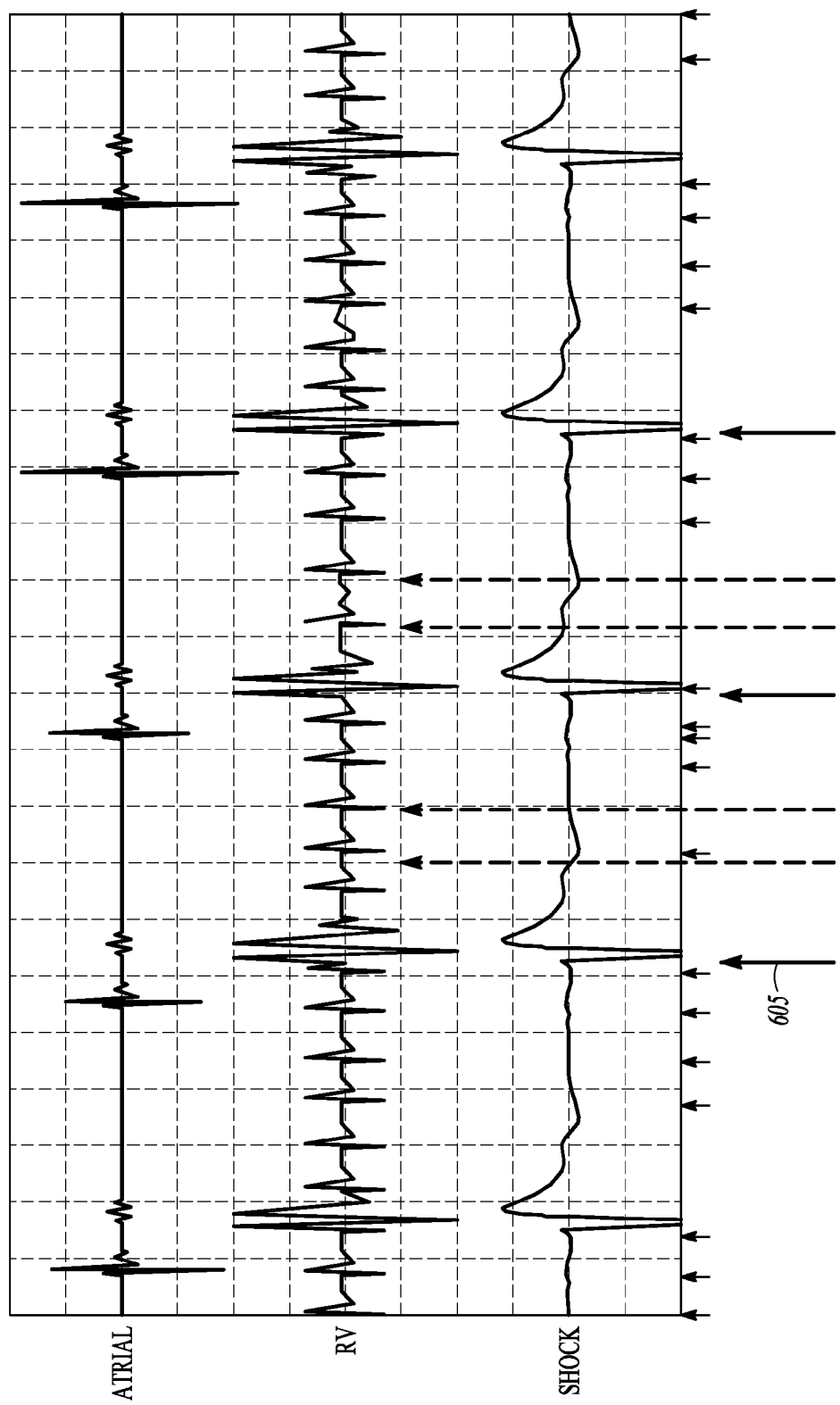
FIG. 6 shows an example of aligning sensed cardiac signal segments.

An illustrative example is shown in FIG. 6. In the example, the primary sensing circuit 505 senses the first cardiac signal using an RV channel and the secondary sensing circuit senses the secondary cardiac signal using a shock channel. Thus, the first cardiac signal and the secondary cardiac signal are sensed using different sense vectors and the signals may need to be aligned. A depolarization 605 in the first cardiac signal is determined from a signal peak. The alignment circuit 520 then identifies a signal peak in the secondary cardiac signal that exceeds a specified threshold signal amplitude value. In some examples, the signal peak of the secondary cardiac signal can be determined as the maximum of the absolute value of the signal amplitude in a specified time window (e.g., 200 ms) centered on the depolarization 605 in the first cardiac signal. The alignment circuit 520 then aligns the identified depolarization in the first cardiac signal with the identified signal peak in the secondary cardiac signal.

In some examples, the signal peak of the secondary cardiac signal can be determined as a measured value of signal amplitude that exceeds a calculated adaptive peak detection threshold value.

Figure 7:
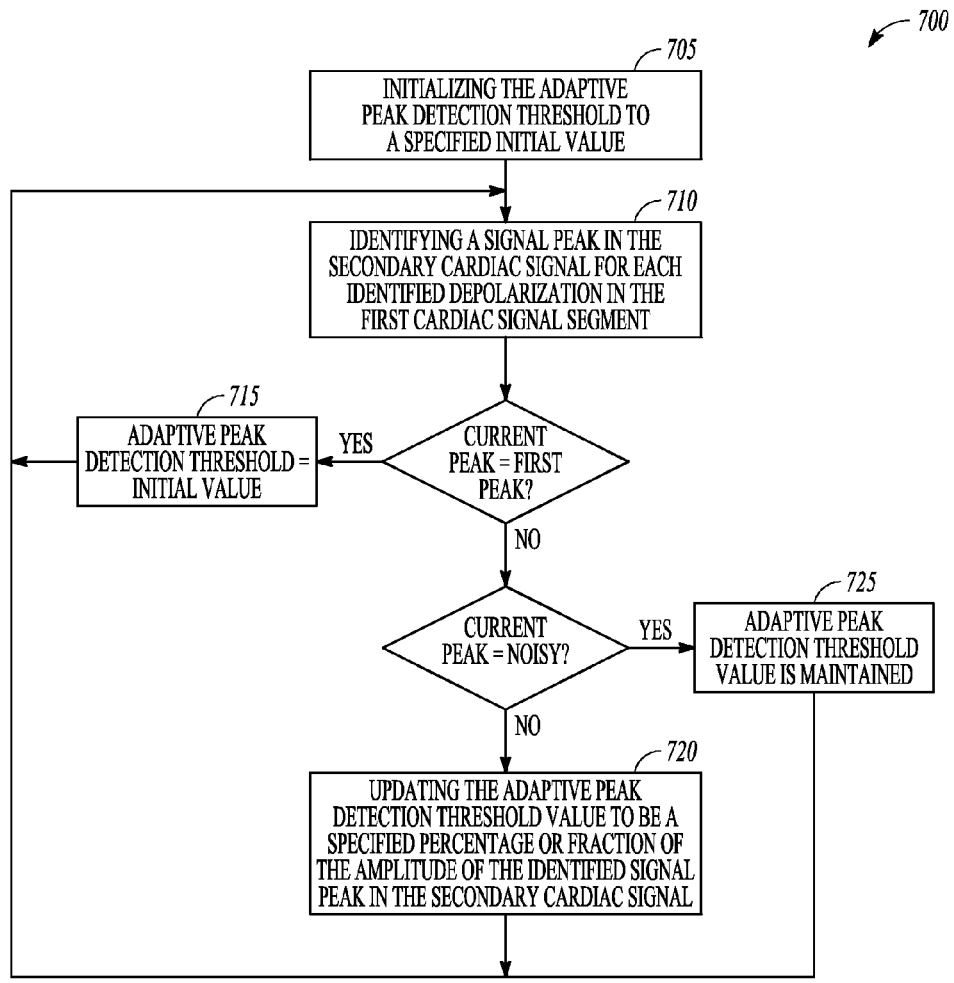
FIG. 7 is a flow diagram of an example of a method of determining an adaptive peak detection threshold.

FIG. 7 is a flow diagram of an example of a method 700 of determining an adaptive peak detection threshold that can be calculated by a device, such as the alignment circuit 520. At block 705, the adaptive peak detection threshold is initialized (e.g., programmed) to an initial value.

At block 710, a signal peak in the secondary cardiac signal is identified for each depolarization identified in the first cardiac signal segment. A signal peak is identified as a peak that exceeds the adaptive peak detection threshold value. If the current depolarization is the first depolarization in the first cardiac signal segment, the default or nominal initial value is used for the detection at block 715. After the first signal peak is identified, the adaptive peak detection threshold used to detect a signal peak in the current depolarization is determined from a previous signal peak of the secondary signal.

At block 720, the adaptive peak detection threshold value is updated to be a specified percentage or fraction (e.g., 60%) of the amplitude of the identified signal peak in the secondary cardiac signal when the secondary signal is determined to be non-noisy. If the secondary signal is determined to be noisy, the current value of the adaptive peak detection threshold value is maintained at block 725, rather than updated.

The described alignment process can also be used to align signals for a morphology analysis. Morphology analysis is an enhancement for tachyarrhythmia detection that compares the sensed arrhythmia to a template of a known morphology (such as normal sinus rhythm or NSR) stored in memory. When the sensed signal and the template are aligned, such as by the method described previously, a coefficient of correlation (e.g., a feature correlation coefficient or FCC) is calculated that is a measure of similarity between the sensed cardiac signal and the template. If the correlation coefficient indicates a high degree of similarity between the sensed cardiac signal and the template of NSR, the sensed rhythm is more likely to be a supraventricular rhythm. For instance, if the calculated value of correlation exceeds a specified correlation threshold value, the sensed arrhythmia is classified as an onset episode of SVT. Examples of methods to discriminate heart rhythms using analysis of the morphology of sensed cardiac signal can be found in Schwartz at al, "Cardiac Rhythm Management Systems and Methods Using Multiple Morphology Templates for Discriminating Between Rhythms," U.S. Pat. No. 7,031,764, filed Nov. 8, 2002 which is incorporated herein by reference in its entirety.

Returning to FIG. 5, the device 500 performs a noise analysis when the signals are aligned. To detect noise, the noise detection circuit 525 determines a number of turns in the first cardiac signal segment and determines a number of turns in the secondary cardiac signal segment. The noise detection circuit 525 generates an indication of noise in the first and secondary cardiac signals according to the determined number of turns.

In some examples, the noise detection circuit 525 includes a turn counter 530 and a timer circuit 535 integral to, or communicatively coupled to, the control circuit 515. The timer circuit 535 is used to establish a specified turn detection timing window in which the noise detection circuit 525 looks for turns. The noise detection circuit 525 identifies a signal turn as a change in direction of the cardiac signal from a positive direction to a negative direction, or from a negative direction to a positive direction. The turn counter 530 is used to track the number of turns and is incremented when identifying a signal turn within the specified turn detection timing window. In some examples, the turn counter 530 only counts turns that exceed a specified (e.g., programmed) turn amplitude threshold. In certain examples, the amplitude of a turn is determined relative to a determined baseline of one or more of the first and secondary cardiac signals. In certain examples, the threshold amplitude is determined as a function of the amplitude of previous identified turns (e.g., within a specified percentage of the amplitude of previous turns). Requiring counted turns to satisfy a threshold can result in the noise detection being less sensitive to low level jitter in the sensed cardiac signals.

Figure 8:
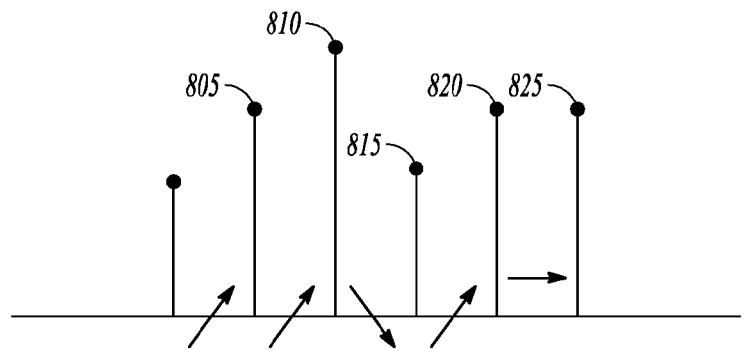
FIG. 8 shows an example of tracking turns in a sensed cardiac signal.

FIG. 8 shows an example of tracking turns in a sensed cardiac signal. The points in the graph represent measured amplitude of data sampled in a cardiac signal. At sample, 810, the signal continues increasing in a positive direction from sample 805 and the turn count is not incremented. At sample 815, the signal direction changed from positive to negative and the noise detection circuit 525 increments the turn count. At sample 820, the signal direction changed from negative to positive and the count is again incremented. At sample 825, the signal amplitude did not change and hence did not change from positive to negative. Consequently, the turn count is not incremented.

The number of turns is tracked for the first cardiac signal and the secondary cardiac signal. In some examples, a cardiac signal is declared noisy when the number of turns in the sampled cardiac signal segment exceeds a specified turn count threshold. In certain examples, the same turn count threshold is used to determine noise in the first and the secondary signal cardiac signal segments. In certain examples, different turn count thresholds are used to determine noise in the signal segments.

In certain examples, the same specified detection timing window is used to determine noise in the first and the secondary signal cardiac signal segments, and in certain examples separate detection windows are used to determine noise in the first and the secondary signal cardiac signal segments. Hence, the noise detection circuit 525 may compare a number of turns identified in a detection window specified for the first cardiac signal segment to a first specified turn count threshold, and compare a number of turns in a detection window specified for the secondary cardiac signal segment to a second specified turn count threshold. The noise detection circuit 525 generates the indication of noise when the number of turns in the first cardiac signal detection timing window and the number of turns in the secondary cardiac signal detection timing window both satisfy their respective turn count threshold.

According to some examples, multiple detection windows are used to detect noise in one or more of the cardiac signal segments. In some examples, the first cardiac signal segment detection timing window includes N detection timing sub-windows, wherein N is a positive integer.

Figure 9:
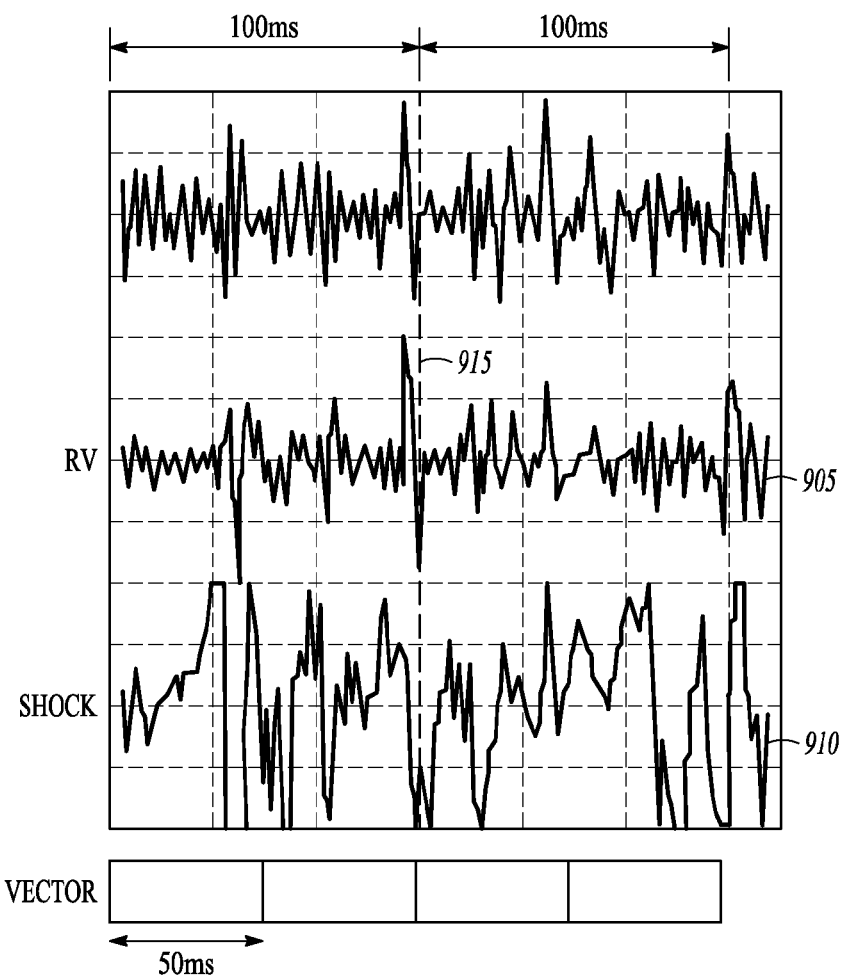
FIG. 9 shows an example of multiple noise detection windows.

FIG. 9 shows an example of multiple noise detection windows where N=4. In the example, the first cardiac signal 905 is sensed using an RV channel and the secondary cardiac signal 910 is sensed using a shock channel. A depolarization 915 is located in the first cardiac signal 905 and the secondary cardiac signal 910 is aligned with the first cardiac signal. A 200 millisecond (ms) detection timing window centered on the depolarization is specified for the secondary cardiac signal and four 50 ms detection timing windows are specified for the first cardiac signal.

The noise detection circuit 525 compares a number of turns in each of the N detection sub-windows to the first specified turn count threshold, and generates the indication of noise when the number of turns in each of the first cardiac signal segment N detection sub-windows satisfies the first specified turn count threshold and the number of turns in the secondary cardiac signal segment detection window satisfies the second specified turn count threshold. For instance, in the example of FIG. 9, noise detection circuit 525 may declare the first cardiac signal to be noisy if the number of turns in the signal in each of the four specified detection timing windows is greater than four turn, and the noise detection circuit 525 may declare the secondary cardiac signal to be noisy if the number of turns in the signal in the 200 ms detection timing window is great than 12. If the number of turns in each window is less than its associated specified threshold number, the beat is determined to be non-noisy.

Other values of turn count thresholds may be specified (e.g., programmed) for the detection windows. In some examples, the turn count threshold for one or more detection windows is specified according to a preference of a caregiver (e.g., the physician). In some examples, the turn count threshold for one or more detection windows is determined (e.g., statistically) from a patient population.

According to some examples, a turn count threshold is adjustable to make the detection more sensitive towards noise and less specific to arrhythmia (e.g., a lower number of turns for a detection window) or to make the detection less sensitive towards noise and more specific to arrhythmia (e.g., a higher number of turns for a detection window).

In some examples, the device 500 adjusts the turn count threshold depending on a patient indicated condition. In some examples, the device 500 includes a memory circuit 540 integral to, or communicatively coupled to, the control circuit 515 to store an indication of pacemaker dependency of the subject. The control circuit 515 adjusts at least one of the first and second specified turn count thresholds according to the indication of pacemaker dependency. For instance, the control circuit 515 may specify a lower number of turns for the turn count threshold to increase sensitivity for a pacemaker dependent patient.

Also, as explained previously, the noise detection circuit may generate the indication of noise according to the result of the alignment of the signals. As an illustrative example, if a cardiac signal segment sensed from the RV channel includes a heartbeat (depolarization) and there is no corresponding heart beat (depolarization) in the cardiac signal segment sensed using a shock channel, then it is very likely that the heartbeat in the RV channel is noise and not a real heartbeat. Had the heartbeat from the RV channel been real, there would have been a corresponding depolarization in the shock channel because the same chamber is being sensed.

If the noise detection circuit 525 determines that the signals are determined to be noisy, it can provide the generated indication of noise to at least one of a user or process. In some examples, the device 500 is an ambulatory device and includes a display. The control circuit 515 may execute a process to display an indication of noise to a user. In some examples, the device 500 is an implantable device and communicates wirelessly with a second device using a communication circuit, such as by RF or inductive telemetry. The second device may have a display to present the indication of noise to a user.

The generated indication of noise can be provided to the control circuit 515 to change or adjust a therapy provided by the device 500. In some examples, the device 500 includes a therapy circuit 545 communicatively coupled to the control circuit 515 to provide electrical pacing therapy. The indication of noise can be used to detect if pacing therapy for bradycardia is incorrectly being withheld due to sensing of noise. The control circuit 515 can determine that noise is continuously indicated on the primary cardiac signal sensing circuit by the noise detection circuit for a specified time duration, and may initiate delivery of pacing therapy when determining that pacing therapy is withheld for the specified time duration.

In some examples, the device 500 includes a therapy circuit 545 communicatively coupled to the control circuit 515 to provide at least one of cardioversion electrical shock therapy, defibrillation electrical shock therapy, and anti-tachyarrhythmia pacing therapy to the subject. The indication of noise can be used to adjust therapy for tachyarrhythmia. The control circuit 515 can include a tachyarrhythmia detection circuit 550 configured to detect tachyarrhythmia using the first cardiac signal. In certain examples, the tachyarrhythmia is detected when depolarizations in the first cardiac signal exceed a specified rate detection threshold. The control circuit 515 can delay delivery of the at least one therapy when the provided indication is that the first cardiac signal segment sensed by the primary cardiac signal sensing circuit is noisy, and initiate delivery of the at least one therapy when the first cardiac signal segment is indicated to be non-noisy.

According to some examples, once the noise detection circuit 525 makes an initial assessment of whether the sensed cardiac signals are noisy, the noise detection circuit 525 may apply a confidence level to the determination. The confidence level can be a measure of the quality of the classification of noise and a measure of whether the output of the noise detection circuit 525 is trustworthy. Application of a confidence level can improve patient treatment in that necessary therapy is less likely to be withheld.

In some examples, the noise detection circuit 525 determines a confidence level of a classification of a cardiac signal segment as being noisy or non-noisy according to the number of turns detected in the first and secondary cardiac signals. The noise detection circuit 525 generates the indication of noise when the number of turns in a cardiac signal segment satisfies a specified turn count threshold and the confidence level of the classification exceeds a specified confidence level threshold value.

In some examples, the confidence level is based on a Gaussian table. An example of a Gaussian table is shown in FIG. 10. The confidence levels (conf) are calculated based on the number of turns (t). FIG. 10 shows an example case where the primary cardiac signal sensing circuit 505 senses includes an RV sense channel and the secondary sensing circuit 510 includes a shock channel. The equations are based on a 200 ms detection window. If the initial determination or classification is that the signals are non-noisy, the confidence in the classification can be calculated using the equation on the left.

For the RV sense channel, the confidence in the classification can be calculated using the equation in the middle. The border line case is 18 turns in the detection window. As the number of turns increases from 18 turns, the calculated confidence that the first cardiac signal is noisy increases. For the shock channel, the confidence in the classification can be calculated using the equation on the right. The border line case is for 13 turns in the detection window. As the number of turns increases from 13 turns, the calculated confidence that the secondary cardiac signal is noisy increases.

In some examples, the memory circuit 540 includes a lookup table of confidence levels stored in association with a number of turns in a cardiac signal segment. For example, the lookup table may store values for confidence levels in association with the detected number of turns, such as is shown in the example of FIG. 10. The noise detection circuit 525 is configured to determine a confidence level, for a noise indication of a cardiac signal segment, from the lookup table according to the number of turns in the cardiac signal segment.

In some examples, the control circuit 515 delays delivery of the at least one therapy when the first cardiac signal segment is indicated to be noisy and a confidence level of the classification exceeds a specified confidence level threshold value. The control circuit 515 initiates delivery of the at least one therapy when at least one of i) the first cardiac signal segment is indicated to be non-noisy, and the first cardiac signal segment is indicated to be noisy, and ii) the confidence level is less than the specified confidence level threshold value.

According to some examples, the device 500 is programmable to provide different modes of operation depending on an assessment of noise. One of the modes is a passive mode in which the device 500 provides an alert when the device 500 detects noise in cardiac signals. If the device 500 is implantable, the alert can be communicated to a second device that may display the indication of noise to a user and/or provide an audible indication of noise.

In some examples, the device 500 can be programmed into an active mode in which the device 500 withholds device therapy if noise is indicated and the determined confidence level in the classification as noise is high (e.g., the confidence level exceeds a threshold). In some examples, the device 500 can be programmed into a semi-active mode in which the device 500 withholds therapy temporarily (e.g., for a specified programmable period of time) if noise is indicated.

Noise in a sensed cardiac signal can come from difference sources, such as a lead fracture, loose set screw, electromagnetic interference (EMI), or an air-bubble near a sensing electrode. According to some examples, the indication of noise can be used by the device 500 to provide (e.g., by display) a cause of the noise to the user. For instance, if the device 500 includes a tachyarrhythmia detection circuit 550, the device 500 may deduce that EMI is causing the sensed signal noise when detecting non-sustained tachyarrhythmia (e.g., tachyarrhythmia that does not last longer than a minimum time duration) and detected R-wave to R-wave depolarization intervals that are less than a specified threshold (e.g., 200 ms).

In another example, the device 500 may include an impedance sensing circuit communicatively coupled to the control circuit 515. An impedance sensing circuit provides current between cardiac electrodes and measures the resulting voltage. The impedance can be determined by the medical device using Ohm's Law (R=V/I). Based on the amount of noise on the primary sensing circuit 505 and a measured impedance of a lead coupled to the primary sensing circuit 505, the device 500 may deduce that the noise is caused by a lead fracture.

Assessing noise with a medical device may result in less over-sensing and under-sensing by the device and lead to improved sensing of events related to cardiac activity. Noise analysis can be performed continuously or periodically (e.g., according to a schedule). The noise detection can be adjusted to be highly specific with respect to arrhythmia and reduce inappropriate therapy, such as inappropriate shocks for example.

Additional Notes

Example 1 includes subject matter (such as an implantable or other ambulatory medical device) comprising a primary cardiac signal sensing circuit, a secondary cardiac signal sensing circuit and a control circuit. The primary cardiac signal sensing circuit is configured to sense at least a first cardiac signal associated with cardiac depolarization, and the primary cardiac signal sensing circuit is to be electrically coupled to at least first and second implantable or wearable electrodes. The secondary cardiac signal sensing circuit is configured to sense a secondary cardiac signal, and the secondary cardiac signal sensing circuit is to be coupled to at least a third electrode different from the first and second electrode.

The control circuit is communicatively coupled to the primary and secondary cardiac signal sensing circuits, and the control circuit includes a noise detection circuit that includes an alignment circuit configured to align a segment of the sensed first cardiac signal with a segment of the sensed secondary cardiac signal, and a turn counter configured to determine a number of turns in the first cardiac signal segment and determine a number of turns in the secondary cardiac signal segment. The noise detection circuit is configured to generate an indication of noise according to at least one of a result of the alignment or the determined number of turns in the first and secondary cardiac signals and provide the indication of noise to a user or process.

In Example 2, the alignment circuit of Example 1 can optionally be configured to identify a depolarization in the first cardiac signal segment, identify a signal peak in the secondary cardiac signal that exceeds a determined adaptive peak detection threshold, and align the identified depolarization in the first cardiac signal with the identified signal peak in the secondary cardiac signal.

In Example 3, the alignment circuit of one or any combination of Examples 1-2 can optionally be configured to initialize the adaptive peak detection threshold to a specified initial value, identify a signal peak in the secondary cardiac signal for each identified depolarization in the first cardiac signal segment, and update the adaptive peak detection threshold value to be a specified percentage or fraction of the amplitude of the identified signal peak in the secondary cardiac signal when the secondary signal is determined to be non-noisy.

In Example 4, the noise detection circuit of one or any combination of Examples 1-3 can optionally include a timer circuit, and the noise detection circuit can optionally be configured identify a signal turn as a change in direction of the cardiac signal from a positive direction to a negative direction or from a negative direction to a positive direction, and increment a turn count when identifying a signal turn within a specified turn detection timing window.

In Example 5, the noise detection circuit of one or any combination of Examples 1-4 can optionally be configured to compare a number of turns identified in a detection timing window specified for the first cardiac signal segment to a first specified turn count threshold, compare a number of turns in a detection timing window specified for the secondary cardiac signal segment to a second specified turn count threshold, and generate the indication of noise when the number of turns in the first cardiac signal detection timing window and the number of turns in the secondary cardiac signal detection timing window both satisfy their respective turn count threshold.

In Example 6, the first cardiac signal segment detection timing window of Example 5 includes N detection timing sub-windows, wherein N is an integer, and the noise detection circuit can optionally be configured to compare a number of turns in each of the N detection sub-windows to the first specified turn count threshold, and generate the indication of noise when the number of turns in each of the first cardiac signal segment N detection sub-windows satisfies the first specified turn count threshold and the number of turns in the secondary cardiac signal segment detection window satisfies the second specified turn count threshold.

In Example 7, the subject matter of one or any combination of Examples, 1-6 optionally includes a memory circuit integral to, or communicatively coupled to, the control circuit and configured to store an indication of pacemaker dependency of the subject. The control circuit can optionally be configured to adjust at least one of the first and second specified turn count thresholds according to the indication of pacemaker dependency.

In Example 8, the noise detection circuit of one or any combination of Examples 1-7 can optionally be configured to determine a confidence level of a classification of a cardiac signal segment as noisy or non-noisy according to the number of turns, and generate the indication of noise when the number of turns in a cardiac signal segment satisfies a specified turn count threshold and the confidence level of the classification exceeds a specified confidence level threshold value.

In Example 9, the subject matter of one or any combination of Examples 1-8 optionally includes a therapy circuit communicatively coupled to the control circuit and configured to provide at least one of cardioversion electrical shock therapy, defibrillation electrical shock therapy, and anti-tachycardia pacing therapy, and the control circuit optionally includes a tachycardia detection circuit configured to detect tachyarrhythmia using the first cardiac signal. The control circuit of Example 8 can optionally be configured to delay delivery of the at least one therapy when the first cardiac signal segment is indicated to be noisy and a confidence level of the classification exceeds a specified confidence level threshold value, and initiate delivery of the at least one therapy when at least one of the first cardiac signal segment is indicated to be non-noisy, or the first cardiac signal segment is indicated to be noisy and the confidence level is less than the specified confidence level threshold value.

In Example 10, the subject matter of one or any combination of Examples 1-9 optionally includes a therapy circuit communicatively coupled to the control circuit and configured to provide at least one of cardioversion electrical shock therapy, defibrillation electrical shock therapy, and anti-tachycardia pacing therapy. The control circuit optionally includes a tachyarrhythmia detection circuit configured to detect tachyarrhythmia using the first cardiac signal, and the control circuit can optionally be configured to delay delivery of the at least one therapy when the first cardiac signal segment sensed by the primary cardiac signal sensing circuit is indicated to be noisy, and initiate delivery of the at least one therapy when the first cardiac signal segment is indicated to be non-noisy.

In Example 11, the subject matter of one or any combination of Examples 1-10 optionally includes a therapy circuit communicatively coupled to the control circuit and configured to provide electrical pacing therapy, and the control circuit can optionally be configured to determine that noise is continuously indicated on the primary cardiac signal sensing circuit by the noise detection circuit for a specified time duration, and initiate delivery of pacing therapy when determining that pacing therapy is withheld for the specified time duration.

In Example 12, the turn counter of one or any combination of Examples 1-11 can optionally be configured to count the number of turns in the first and secondary cardiac signals that exceed a specified turn amplitude threshold.

Example 13 can include subject matter, or can optionally be combined with the subject matter of one or any combination of Examples 1-12 to include subject matter, (such as a method, a means for performing acts, or a machine-readable medium including instructions that, when performed by the machine, cause the machine to perform acts) comprising sensing a first cardiac signal associated with depolarization of a heart using a primary sensing circuit of an implantable or other ambulatory medical device, the primary sensing circuit to be coupled to a first and a second implantable or wearable electrode, sensing a secondary cardiac signal using a secondary sensing circuit, the secondary sensing circuit to be coupled to at least a third electrode different from the first and second electrode, aligning a segment of the first cardiac signal with a segment of the secondary cardiac signal, determining a number of turns in the first cardiac signal segment and determining a number of turns in the secondary cardiac signal segment, generating an indication of noise according to at least one of a result of the aligning or the determined number of turns in the first and secondary cardiac signals, and providing the indication of noise to a user or process.

Such subject matter can include means for sensing a first cardiac signal associated with depolarization of a heart, illustrative examples of which can include one or more implantable electrodes in communication with one or more sense amplifiers, one or more wearable electrodes in communication with one or more sense amplifiers, one or more surface electrodes in communication with one or more sense amplifiers, one or more implantable, wearable or surface electrodes electrically coupled to one or more implantable or wearable cardiac leads, and one or more electrodes formed on a housing of an implantable or other ambulatory medical device.

Such subject matter can include means for sensing a secondary cardiac signal associated with depolarization of a heart, illustrative examples of which can include one or more implantable electrodes in communication with one or more sense amplifiers, one or more wearable electrodes in communication with one or more sense amplifiers, one or more surface electrodes in communication with one or more sense amplifiers, one or more implantable, wearable or surface electrodes electrically coupled to one or more implantable or wearable cardiac leads, and one or more electrodes formed on a housing of an implantable or other ambulatory medical device.

Such subject matter can include means for aligning a segment of the first cardiac signal with a segment of the secondary cardiac signal, illustrative examples of which can include a control circuit, such as a processor, having an alignment circuit configured by one or more of hardware, software, and firmware to perform the aligning.

Such subject matter can include means for determining a number of turns in the first cardiac signal segment and determining a number of turns in the secondary cardiac signal segment, illustrative examples of which can include a control circuit, such as a processor, having a noise detection circuit configured by one or more of hardware, software, and firmware and having a turn counter to perform the determining.

Such subject matter can include means for generating an indication of noise according to at least one of a result of the aligning or the determined number of turns in the first and secondary cardiac signals, illustrative examples of which can include a control circuit, such as a processor, having a noise detection circuit configured by one or more of hardware, software, and firmware to perform the generating.

Such subject matter can include means for providing the indication of noise to a user or process, illustrative examples of which can include a display, a wireless communication circuit, and an indication (e.g., a signal) communicated to the control circuit.

In Example 14, the aligning a segment of the first cardiac signal with a segment of the secondary cardiac signal of Example 13 can optionally include identifying a depolarization in the first cardiac signal segment, identifying a signal peak in the secondary cardiac signal that exceeds a determined adaptive peak detection threshold, and aligning the identified depolarization in the first cardiac signal with the identified signal peak in the secondary cardiac signal.

In Example 15, the determining an adaptive peak detection threshold of Example 14 can optionally include initializing the adaptive peak detection threshold to a specified initial value, identifying a signal peak in the secondary cardiac signal for each identified depolarization in the first cardiac signal segment, and updating, for each identified depolarization in the first cardiac signal segment, the adaptive peak detection threshold value to be a specified percentage or fraction of the amplitude of the identified signal peak in the secondary cardiac signal when the secondary signal is determined to be non-noisy.

In Example 16, the determining a number of turns in a cardiac signal segment of one or any combination of Example 13-15 can optionally include identifying a signal turn as a change in direction of the cardiac signal from a positive direction to a negative direction or from a negative direction to a positive direction, and incrementing a turn count when identifying a signal turn within a specified turn detection timing window.

In Example 17, the generating an indication of noise in the first and secondary cardiac signals, according to the determined number of turns, of one or any combination of Examples 13-16 can optionally include comparing a number of turns identified in a detection window specified for the first cardiac signal segment to a first specified turn count threshold, comparing a number of turns in a detection window specified for the secondary cardiac signal segment to a second specified turn count threshold; and generating the indication of noise when the number of turns in the first cardiac signal detection window and the number of turns in the secondary cardiac signal detection window both satisfy their respective turn count threshold.

In Example 18, the generating an indication of noise of one or any combination of Examples 13-17 can optionally include determining a confidence level of a classification of a cardiac signal segment as noisy or non-noisy according to the number of turns and generating the indication of noise when the number of turns in a cardiac signal segment satisfies a specified turn count threshold and the confidence level of the classification exceeds a specified confidence level threshold value.

In Example 19, the subject matter of one or any combination of Examples 13-18 can optionally include detecting tachycardia using the first cardiac signal, delaying delivery of one or more of cardioversion/defibrillation therapy and anti-tachycardia pacing therapy by the medical device when at least one of the first cardiac signal segment or the secondary cardiac signal segment are indicated to be noisy, and initiating delivery of cardioversion/defibrillation therapy by the medical device when neither the first cardiac signal segment or the secondary cardiac signal segment are indicated to be noisy.

In Example 20, the subject matter of one or any combination of Examples 1-19 can optionally include determining that noise is continuously indicated on the primary sensing circuit for a specified time duration, and initiating delivery of pacing therapy when determining that pacing therapy is withheld for the specified time duration.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An implantable or other ambulatory medical device comprising:
   a primary cardiac signal sensing circuit configured to sense at least a first cardiac signal associated with cardiac depolarization, the primary cardiac signal sensing circuit configured to be electrically coupled to at least first and second implantable or wearable electrodes;
   a secondary cardiac signal sensing circuit configured to sense a secondary cardiac signal, the secondary cardiac signal sensing circuit to be coupled to at least a third electrode different from the first and second electrode; and
   a control circuit, communicatively coupled to the primary and secondary cardiac signal sensing circuits, the control circuit including a noise detection circuit that includes:
      an alignment circuit configured to align a segment of the sensed first cardiac signal with a segment of the sensed secondary cardiac signal; and
      a turn counter configured to:
         determine a number of turns in the first cardiac signal segment; and
         determine a number of turns in the secondary cardiac signal segment;
      wherein the noise detection circuit is configured to
         identify a signal turn as a change in direction of the cardiac signal from a positive direction to a negative direction or from a negative direction to a positive direction;
         increment a turn count when identifying a signal turn within a specified turn detection timing window;
         compare a number of turns identified in a detection timing window specified for the first cardiac signal segment to a first specified turn count threshold;
         compare a number of turns in a detection timing window specified for the secondary cardiac signal segment to a second specified turn count threshold; and
         generate the indication of noise when the number of turns in the first cardiac signal detection timing window and the number of turns in the secondary cardiac signal detection timing window both satisfy their respective turn count threshold; and
         provide the indication of noise to a user or process.

2. The device of claim 1, wherein the alignment circuit is configured to:
   identify a depolarization in the first cardiac signal segment;
   identify a signal peak in the secondary cardiac signal that exceeds a determined adaptive peak detection threshold; and
   align the identified depolarization in the first cardiac signal with the identified signal peak in the secondary cardiac signal.

3. The device of claim 2, wherein the alignment circuit is configured to:
   initialize the adaptive peak detection threshold to a specified initial value;
   identify a signal peak in the secondary cardiac signal for each identified depolarization in the first cardiac signal segment; and
   update the adaptive peak detection threshold value to be a specified percentage or fraction of the amplitude of the identified signal peak in the secondary cardiac signal when the secondary signal is determined to be non-noisy.

4. The device of claim 1,
   wherein the first cardiac signal segment detection timing window includes N detection timing sub-windows, wherein N is an integer, and
   wherein the noise detection circuit is configured to:
   compare a number of turns in each of the N detection sub-windows to the first specified turn count threshold; and
   generate the indication of noise when the number of turns in each of the first cardiac signal segment N detection sub-windows satisfies the first specified turn count threshold and the number of turns in the secondary cardiac signal segment detection window satisfies the second specified turn count threshold.

5. The device of claim 1, including:
   a memory circuit integral to, or communicatively coupled to, the control circuit and configured to store an indication of pacemaker dependency of the subject,
   wherein the control circuit is configured to adjust at least one of the first and second specified turn count thresholds according to the indication of pacemaker dependency.

6. The device of claim 1, wherein the noise detection circuit is configured to:
   determine a confidence level of a classification of a cardiac signal segment as noisy or non-noisy according to the number of turns; and
   generate the indication of noise when the number of turns in a cardiac signal segment satisfies a specified turn count threshold and the confidence level of the classification exceeds a specified confidence level threshold value.

7. The device of claim 6, including:
   a therapy circuit communicatively coupled to the control circuit and configured to provide at least one of cardioversion electrical shock therapy, defibrillation electrical shock therapy, and anti-tachycardia pacing therapy;
   wherein the control circuit includes a tachycardia detection circuit configured to detect tachyarrhythmia using the first cardiac signal, and
   wherein the control circuit is configured to:
   delay delivery of the at least one therapy when the first cardiac signal segment is indicated to be noisy and a confidence level of the classification exceeds a specified confidence level threshold value; and
   initiate delivery of the at least one therapy when at least one of:
      the first cardiac signal segment is indicated to be non-noisy; or
      the first cardiac signal segment is indicated to be noisy and the confidence level is less than the specified confidence level threshold value.

8. The device of claim 1, including:
   a therapy circuit communicatively coupled to the control circuit and configured to provide at least one of cardioversion electrical shock therapy, defibrillation electrical shock therapy, and anti-tachycardia pacing therapy;
   wherein the control circuit includes a tachyarrhythmia detection circuit configured to detect tachyarrhythmia using the first cardiac signal, and
   wherein the control circuit is configured to:
   delay delivery of the at least one therapy when the first cardiac signal segment sensed by the primary cardiac signal sensing circuit is indicated to be noisy; and initiate delivery of the at least one therapy when the first cardiac signal segment is indicated to be non-noisy.

9. The device of claim 1, including:
a therapy circuit communicatively coupled to the control circuit and configured to provide electrical pacing therapy, and
wherein the control circuit is configured to:
determine that noise is continuously indicated on the primary cardiac signal sensing circuit by the noise detection circuit for a specified time duration; and
initiate delivery of pacing therapy when determining that pacing therapy is withheld for the specified time duration.

10. The device of claim 1, wherein the turn counter is configured to count the number of turns in the first and secondary cardiac signals that exceed a specified turn amplitude threshold.

11. The device of claim 1, wherein the noise detection circuit is configured to generate an indication of noise according to the determined number of turns in the first and secondary cardiac signals.

12. The device of claim 1, wherein the noise detection circuit is configured to generate an indication of noise according to the result of the alignment of the first and secondary cardiac signals.

13. A method comprising:
sensing a first cardiac signal associated with depolarization of a heart using a primary sensing circuit of an implantable or other ambulatory medical device, the primary sensing circuit to be coupled to a first and a second implantable or wearable electrode;
sensing a secondary cardiac signal using a secondary sensing circuit, the secondary sensing circuit to be coupled to at least a third electrode different from the first and second electrode;
aligning a segment of the first cardiac signal with a segment of the secondary cardiac signal;
determining a number of turns in the first cardiac signal segment and determining a number of turns in the secondary cardiac signal segment, wherein determining a number of turns in a cardiac signal segment includes identifying a signal turn as a change in direction of the cardiac signal from a positive direction to a negative direction or from a negative direction to a positive direction, and incrementing a turn count when identifying a signal turn within a specified turn detection timing window;
comparing a number of turns identified in a detection window specified for the first cardiac signal segment to a first specified turn count threshold;
comparing a number of turns in a detection window specified for the secondary cardiac signal segment to a second specified turn count threshold; and
generating the indication of noise when the number of turns in the first cardiac signal detection window and the number of turns in the secondary cardiac signal detection window both satisfy their respective turn count threshold; and
providing the indication of noise to a user or process.

14. The method of claim 13, wherein aligning a segment of the first cardiac signal with a segment of the secondary cardiac signal includes:
identifying a depolarization in the first cardiac signal segment;
identifying a signal peak in the secondary cardiac signal that exceeds a determined adaptive peak detection threshold; and
aligning the identified depolarization in the first cardiac signal with the identified signal peak in the secondary cardiac signal.

15. The method of claim 14, wherein determining an adaptive peak detection threshold includes:
initializing the adaptive peak detection threshold to a specified initial value;
identifying a signal peak in the secondary cardiac signal for each identified depolarization in the first cardiac signal segment; and
updating, for each identified depolarization in the first cardiac signal segment, the adaptive peak detection threshold value to be a specified percentage or fraction of the amplitude of the identified signal peak in the secondary cardiac signal when the secondary signal is determined to be non-noisy.

16. The method of claim 13, wherein generating an indication of noise includes:
determining a confidence level of a classification of a cardiac signal segment as noisy or non-noisy according to the number of turns; and
generating the indication of noise when the number of turns in a cardiac signal segment satisfies a specified turn count threshold and the confidence level of the classification exceeds a specified confidence level threshold value.

17. The method of claim 16, including:
detecting tachycardia using the first cardiac signal;
delaying delivery of one or more of cardioversion/defibrillation therapy and anti-tachycardia pacing therapy by the medical device when at least one of the first cardiac signal segment or the secondary cardiac signal segment are indicated to be noisy; and
initiating delivery of cardioversion/defibrillation therapy by the medical device when neither the first cardiac signal segment or the secondary cardiac signal segment are indicated to be noisy.

18. The method of claim 13, including:
determining that noise is continuously indicated on the primary sensing circuit for a specified time duration; and
initiating delivery of pacing therapy when determining that pacing therapy is withheld for the specified time duration.

* * * * *